(12) United States Patent
Chasan

(10) Patent No.: US 11,484,430 B2
(45) Date of Patent: Nov. 1, 2022

(54) COMPRESSIVE NASAL DEVICE AND METHOD FOR USING THE SAME

(71) Applicant: Paul E. Chasan MD Inc., Del Mar, CA (US)

(72) Inventor: Paul E. Chasan, Del Mar, CA (US)

(73) Assignee: Paul E. Chasan MD Inc., Del Mar, CA (US)

( * ) Notice: Subject to any disclaimer, the term of this patent is extended or adjusted under 35 U.S.C. 154(b) by 227 days.

(21) Appl. No.: 17/063,970

(22) Filed: Oct. 6, 2020

(65) Prior Publication Data

US 2022/0104961 A1 Apr. 7, 2022

(51) Int. Cl.
*A61F 5/08* (2006.01)

(52) U.S. Cl.
CPC ..................... *A61F 5/08* (2013.01)

(58) Field of Classification Search
CPC .......... A61F 5/56; A61F 5/05891; A61F 5/08; A61F 2/186; A61B 17/122; A61B 17/083
USPC .......................................................... 606/199
See application file for complete search history.

(56) References Cited

U.S. PATENT DOCUMENTS

| | | | |
|---|---|---|---|
| 2,398,073 A | 4/1946 | Bonde | |
| 3,935,859 A | 2/1976 | Doyle | |
| 4,213,452 A | 7/1980 | Shippert | |
| 4,274,402 A | 6/1981 | Shippert | |
| 4,378,802 A | 4/1983 | Ersek | |
| 4,402,314 A | 9/1983 | Goode | |
| 4,592,357 A | 6/1986 | Ersek | |
| 4,774,935 A | 10/1988 | Aronsohn | |
| 5,284,469 A | 2/1994 | Jasen | |
| 5,383,891 A | 1/1995 | Walker | |
| 5,669,377 A | 9/1997 | Fenn | |
| 5,769,089 A | 6/1998 | Hand | |
| 5,817,039 A | 10/1998 | Rauning | |
| 5,961,537 A | 10/1999 | Gould | |
| 5,989,270 A * | 11/1999 | Suh | A61F 5/08 606/157 |
| 7,105,008 B2 | 9/2006 | Maryanka | |
| 8,092,478 B2 | 1/2012 | Kotler | |
| 8,801,751 B2 | 8/2014 | Kaczperski | |
| 8,858,477 B2 | 10/2014 | Pylyp | |
| 9,421,120 B2 | 8/2016 | Obando | |
| 2010/0042139 A1 | 2/2010 | Honegger | |
| 2011/0106140 A1 | 5/2011 | Obando | |

(Continued)

*Primary Examiner* — Majid Jamialahmadi
(74) *Attorney, Agent, or Firm* — Marcus C. Dawes

(57) ABSTRACT

A nasal compressive device for preventing post-operative swelling following a rhinoplasty or other procedure performed on a user's nose or nasal cavity and prevent possible poly-beak deformities. The nasal compressive device includes nasal plugs and a nasal bridge disposed on a selectively actuated clip with a resilient spring portion. The user actuates the clip to open the nasal compressive device and then inserts the nasal plugs into their nostrils. The user then relaxes or closes the nasal compressive device which brings the nasal plugs into contact with an inner surface of their nasal cavity while also forcing the nasal bridge down on top of the user's dorsum. Once placed in the user's nose, the nasal compressive device also applies an upward force to the tip of the user's nose while also simultaneously providing a compression force over the user's dorsum, thereby reducing the amount of unwanted swelling and further shaping the nose.

19 Claims, 3 Drawing Sheets

(56) References Cited

U.S. PATENT DOCUMENTS

2011/0270297 A1 11/2011 Judd
2012/0022582 A1 1/2012 Guyuron

* cited by examiner

COMPRESSIVE NASAL DEVICE AND METHOD FOR USING THE SAME

BACKGROUND

Field of the Technology

The invention relates to the field of nasal splints, compression devices and shapers, and in particular to nasal compression devices which provide a compressive force to the supratip of a patient's nose while also elevating the lower nasal cartilage of a patient so as to prevent the development of scar tissue in the middle and distal portions of the patient's nasal dorsum.

Description of the Prior Art

Rhinoplasty continues to be one of the most common aesthetic surgeries performed around the world. It requires surgically shaping and contouring the underlying bony and cartilaginous structures and having the skin envelope adapt to those new contours of the nose.

One of the most common complications associated with rhinoplasty surgery is the development of scar tissue and swelling in the "supratip" area which is the distal third of the nasal dorsum j List above the nasal tip. Clinically, this is known as a "poly-beak" deformity. This is especially common in patients who have thick skin and/or larger reductions in the nasal structures. Until now, the most common ways to prevent this would be to "night tape" which requires the patient to apply tape every night across the nose to the cheeks to add pressure and compress the soft tissues of this portion of the nose. Generally, it is not that easy to perform, not particularly effective, and causes a lot of irritation to the cheek skin. Because of this, the patient compliance is low and the effectiveness is only adequate; however, it is better than doing nothing.

Others in the art have developed head straps in which a strap is placed around the back of the head or neck and applies a pressure to a splint that compresses the supratip. These are bulky, very uncomfortable, and tend to slip thereby not applying pressure to the correct areas. Again, the compliance is low. Ultimately, many plastic surgeons will then inject a steroid into the supratip area to remedy the situation. This requires injecting with a needle, has unpredictable results, and can have significant complications.

Additionally, there are many different varieties of nasal shaping devices, however almost every one of them is used to narrow the nose. One such nasal split comprises multiple layers which are placed over the outs ide surface of the patient's nose in succession, namely an adhesive or base layer followed by one or more flexible interstitial layers which is then followed or capped by a semi-rigid metallic or support layer which protects the patient's nasal pyramid from the outside environment.

Another type of nasal splint used in the prior art comprises a support which fits over the patient's nasal pyramid, the support being configured to accommodate a plurality of compression heads therein. The position of each compression head may be adjusted to fit the needs of each unique patient and then selectively actuated to provide a desired amount compression directly to the patient's nasal bridge. While capable of delivering a certain amount of compression to the patient, such splints however also require a band which must fit around the patient's entire head and face which can be uncomfortable and which can also lead to reduced patient compliance. Additionally, the compression heads are used to further narrow the nose, not for preventing complications associated with rhinoplasty, namely the development of scar tissue and swelling in the "supratip" area of the patient's nose.

What is needed therefore is a nasal compressive device which is a simple, easy-to-use, device which comprises the ability to apply direct pressure to the supratip area that would be comfortable, effective, and increase patient compliance.

BRIEF SUMMARY

The current invention of provides a nasal shaping device specifically used to diminish swelling in the supratip area and elevate the nasal tip. Additionally, the current invention can be used to shape the nose and create a subtle tip elevation. In today's world with COVID-19, most people are wearing masks which tend to push down on the tip of the nose and stretch the underlying soft tissues giving a subtle droopiness to the nasal tip. The device of the current invention could be used to reverse the effects of chronic mask wearing.

The current invention provides a nasal compressive device which includes a clip, a nasal bridge disposed on a first segment of the clip, a plurality of nasal plugs disposed on a second segment of the clip, and/or a spring portion disposed between the first and second segments. The spring portion is specifically configured to push the nasal plugs and the nasal bridge together when it is in an expanded configuration.

In one embodiment, the plurality of nasal plugs disposed on the second segment of the clip are specifically disposed at an angle relative to each other.

In another embodiment, each of the plurality of nasal plugs of the nasal compressive device has a longitudinal axis that is disposed parallel relative to each other.

In yet another embodiment, each of the plurality of nasal plugs of the nasal compressive device has a tapered shape. Specifically, each nasal plug has a smaller cross-sectional width at its distal end as compared to its proximal end.

In a further embodiment, the nasal bridge disposed on the first segment of the clip is specifically configured to accommodate a nasal dorsum of a user.

In another embodiment, the nasal compressive device also includes a plurality of finger grips that are disposed on the clip. Specifically, at least one of the plurality of finger grips is disposed between the first segment of the clip and the spring portion, while at least another one of the plurality of finger grips is disposed between the second segment of the clip and the spring portion.

In a further embodiment, the nasal compressive device also includes a pivot point that is disposed on the first segment of the clip so that the nasal bridge is rotatably coupled to the first segment of the clip through the pivot point.

The invention also provides a method of providing support to the nose of a user recovering from a medical procedure. The method includes opening a nasal compressive device, inserting a pair of nasal plugs disposed on the nasal compressive device into a corresponding pair of nostrils of the user's nose, and closing the nasal compressive device over the nose of the user. Next, an upwardly directed force is applied to a lower nasal cartilage portion of the user's nose.

In one embodiment, the method also includes applying a compressive force to a dorsum portion of the user's nose. The compressive force and the upwardly directed force may be simultaneously applied to the dorsum portion and the lower nasal portion of the user's nose, respectively. In a related embodiment, applying the compressive force to the dorsum portion of the user's nose is accomplished by pressing a nasal bridge disposed on the nasal compressive device against the dorsum portion of the user's nose. Compressing the spring portion may be done by squeezing a pair of finger grips together, wherein each of the pair of finger grips correspond to the first segment and the second segment of the nasal compressive device, respectively.

In another embodiment, opening the nasal compressive device is done by compressing a spring portion disposed within the nasal compressive device and then separating a nasal bridge disposed on a distal end of a first segment of the nasal compressive device from the pair of nasal plugs disposed on a distal end of a second segment of the nasal compressive device. An angle of the nasal bridge relative to a first segment of the nasal compressive device may also be selectively adjusted or changed.

In a further embodiment, applying the upwardly directed force to the lower nasal cartilage portion of the user's nose includes pressing each of the nasal plugs against an inner surface of a nasal cavity of the user. In a related embodiment, the step of pressing the nasal bridge disposed on the nasal compressive device against the dorsum portion of the user's nose further includes expanding a spring portion of the nasal compressive device disposed between the nasal bridge and the pair of the nasal plugs.

In yet another embodiment, closing the nasal split includes expanding a spring disposed on the nasal compressive device which brings a nasal bridge disposed on a distal end of a first portion of the nasal compressive device closer together to the pair of nasal plugs disposed on a distal end of a second portion of the nasal compressive device.

In a further embodiment, inserting the pair of nasal plugs disposed on the nasal compressive device into a corresponding pair of nostrils of the user's nose specifically includes inserting a pair of parallel nasal inserts into the corresponding pair of nostrils of the user's nose.

In one specific embodiment, inserting, the pair of nasal plugs disposed on the nasal compressive device into a corresponding pair of nostrils of the user's nose includes inserting at least one of the pair of nasal plugs into at least of one of the pair of nostrils at an angle relative to the remaining one of the pair of nasal plugs.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
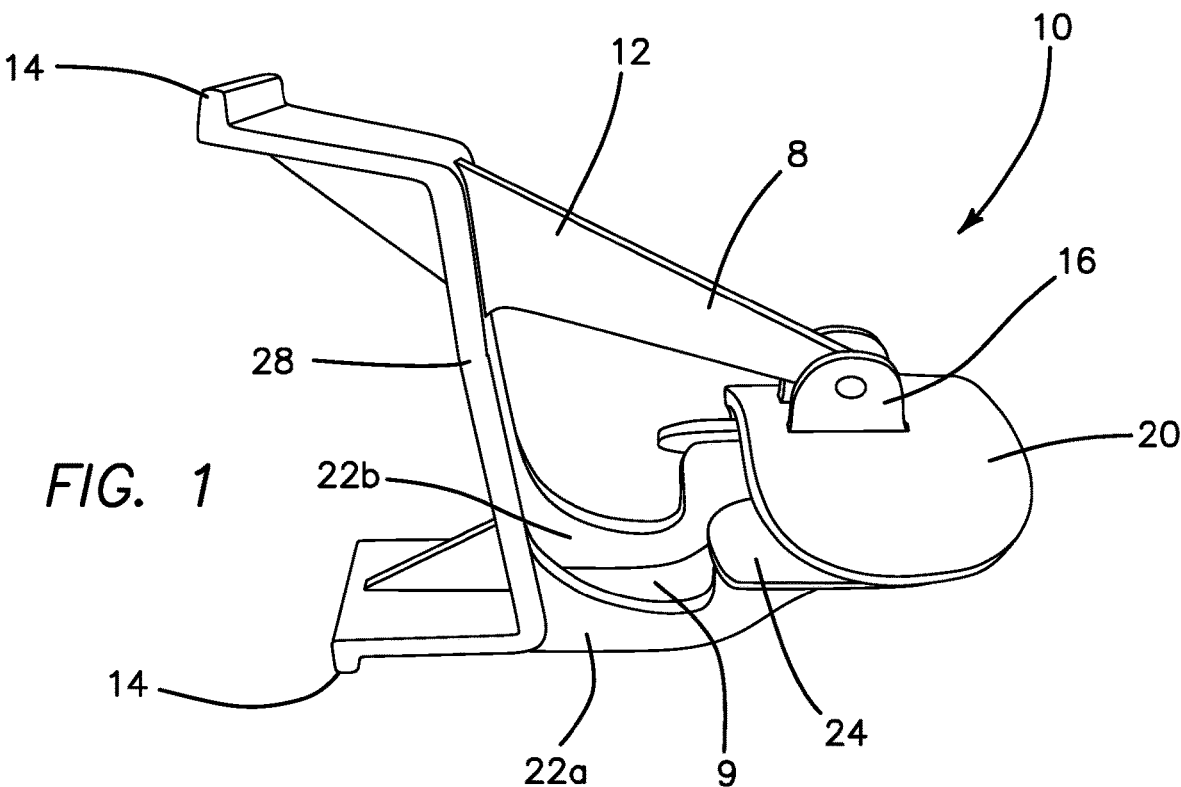
FIG. 1 is a side view of the nasal compressive device of the current invention while the nasal compressive device is in the closed position.
Figure 2:
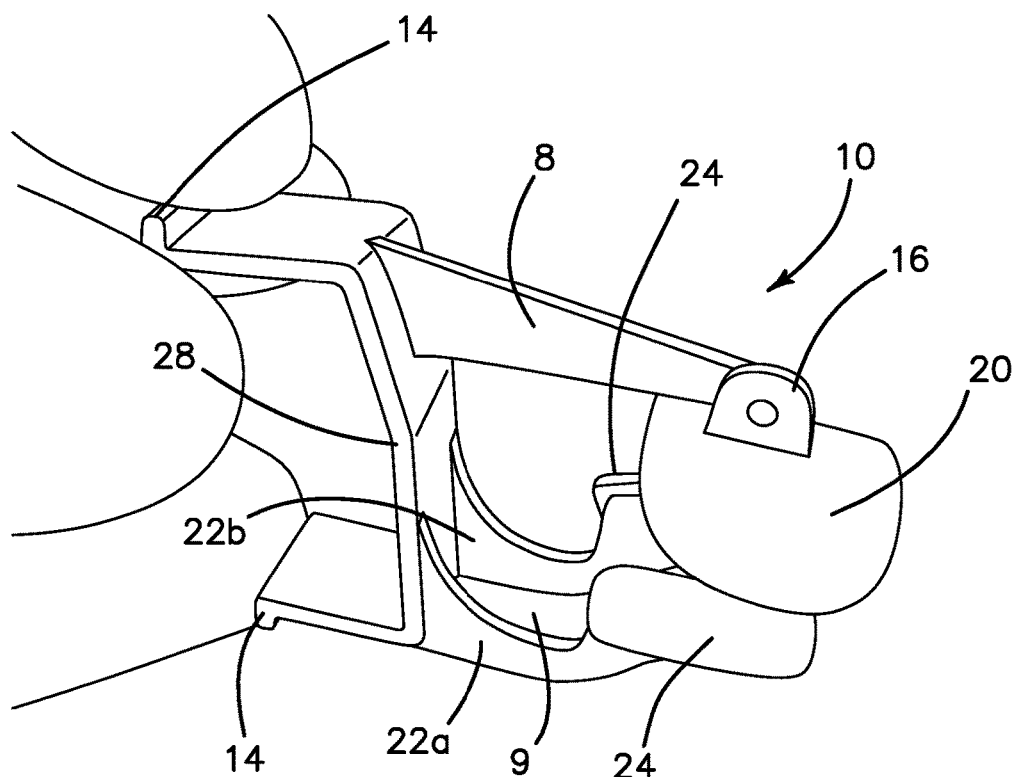
FIG. 2 is a side view of the nasal compressive device seen in FIG. 1 as a user actuates the nasal compressive device to open the nasal compressive device.
Figure 3:
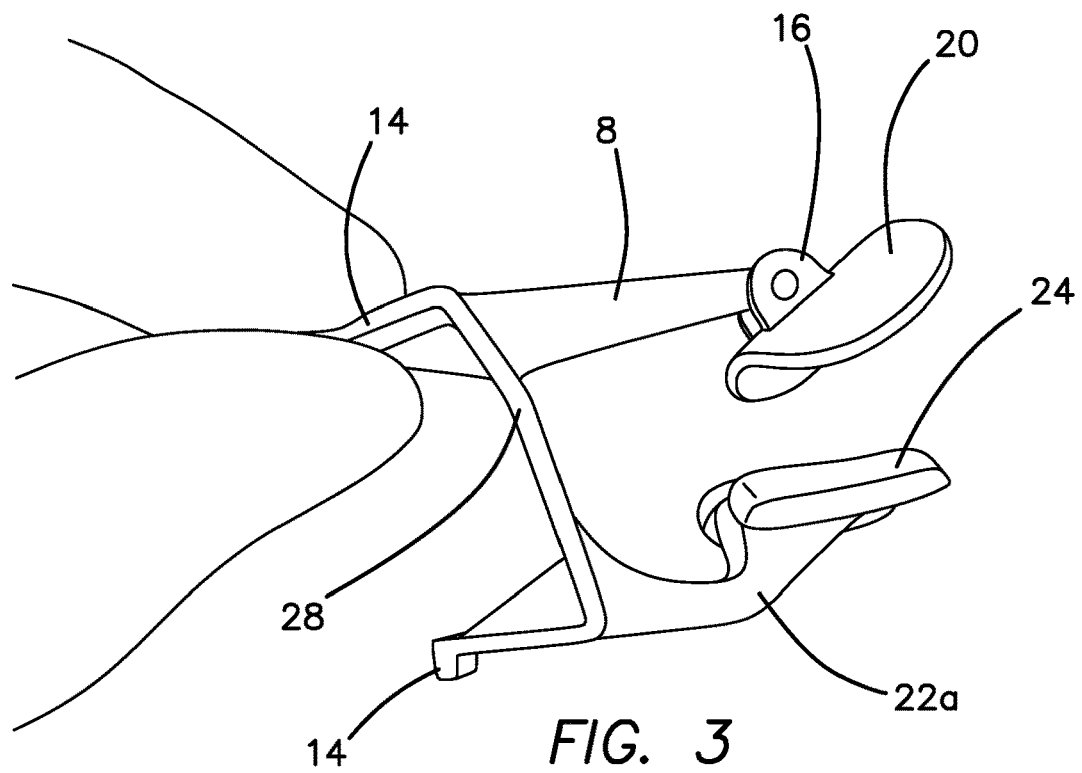
FIG. 3 is a side view of the nasal compressive device seen in FIG. 2 while the nasal compressive device is in the open position.

The current invention is a nasal compressive device which is shown in detail in FIGS. 1-4 and which is denoted generally by reference numeral 10. The nasal compressive device 10 comprises a substantially wedge-shaped clip 12 which is comprised of a pair of finger grips 14 that are disposed on a pair of opposing segments of the clip 12, namely a bridge segment 8 and a nostril segment 9 joined together by a resilient spring portion 28. The bridge segment 8 and the nostril segment 9 are orientated to face each other in a substantially mirror-image configuration. The spring portion 28 is specifically disposed between the bridge segment 8 and the nostril segment 9, namely at where each of the finger grips 14 meet the remainder of the clip 12. The clip 12 is preferably comprised of plastic, plastic composites, or other resilient yet substantially flexible material so that the spring portion 28 may be deformed by the user as seen in FIG. 3 and then automatically return or conform to its original shape best seen in FIGS. 1 and 2 when user releases the clip 12 as detailed below. In a related embodiment, the spring portion 28 may comprise a segment or portion of material which is different than the remaining portions or parts of the clip 12. Specifically, the spring portion 28 may comprise a portion of material which comprises a different degree of flexibility relative to the remaining portions of the clip 12 so as to provide a more robust spring constant. Alternatively, the spring portion 28 may also comprise a hinge, a pivot point, or other structural equivalent which assists the spring portion 28 in opening or closing the nasal compressive device 10.

Figure 4:
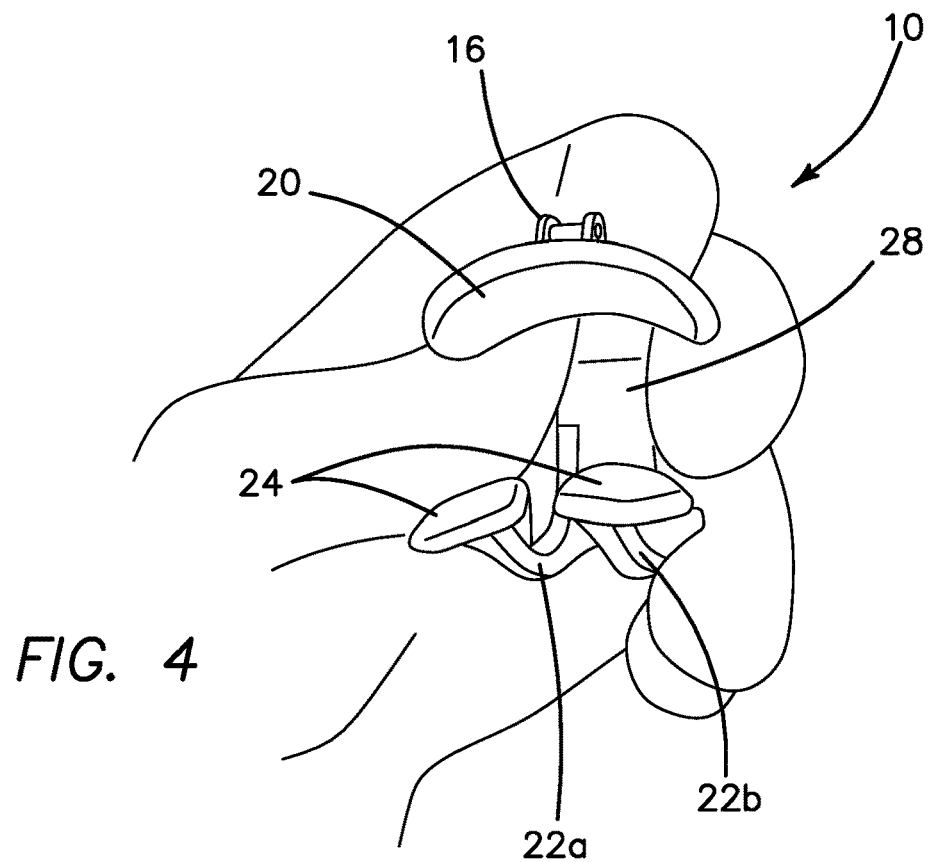
FIG. 4 is a frontal view of the nasal compressive device seen in FIG. 3 while the nasal compressive device is in the open position.

As best seen in FIGS. 1 and 2, the nostril segment 9 comprises a pair of nasal inserts 22a, 22b that are substantially parallel respective to each other while the bridge segment 8 comprises a curved nasal bridge 20 coupled to the bridge segment 8 via a pivot point 16. The nasal bridge 20 comprises a positive curvature as seen the frontend view of FIG. 4. Disposed or coupled onto each of the nasal inserts 22a, 22b are a corresponding pair of nasal plugs 24. The nasal plugs 24 are each substantially tear drop shaped, oval shaped, or otherwise comprise a tapered width so as to easily and comfortably be inserted into the nostrils of a user as is discussed further below. Both the nasal plugs 24 are preferably comprised of a soft, malleable material such as rubber, silicone, neoprene, or other similar materials now known or later devised. Each of the nasal plugs 24 are disposed or orientated at an angle relative to each other with each nasal plug 24 being specifically angled or tilted towards away from one another as best seen in FIG. 4. The nasal plugs 24 may further comprise an additional layer or soft padding which may be selectively coupled to each nasal plug 24 to provide additional resiliency or comfort for users may have a larger nose or nostrils.

To actuate or use the nasal compressive device 10, a user 30 places a finger or thumb on either one or both of the finger grips 14 as seen in FIG. 3 and moves or squeezes the finger grips 14 together which in turn compresses the spring portion 28 disposed there between. As the user continues to squeeze, the proximal ends of the bridge segment 8 and the nostril segment 9 are brought closer together which in turn separate the nasal bridge 20 from the nasal plugs 24 and open the nasal compressive device 10. When the user 30 releases or relaxes the pressure placed on the finger grips 14 the inherent resiliency or spring constant of the spring portion 28 brings the bridge segment 8 and nostril segment 9 back closer together until contact is made between the upward facing surface of the nasal plugs 24 and the nasal bridge 20 thereby closing the nasal compressive device 10. The user 30 may repeatedly open and close the nasal compressive device 10 in the above manner whenever treatment is required thereby allowing the user 30 to selectively apply the nasal compressive device 10 according to a specific treatment regimen, for example when the user 30 is to go to bed.

Figure 5:
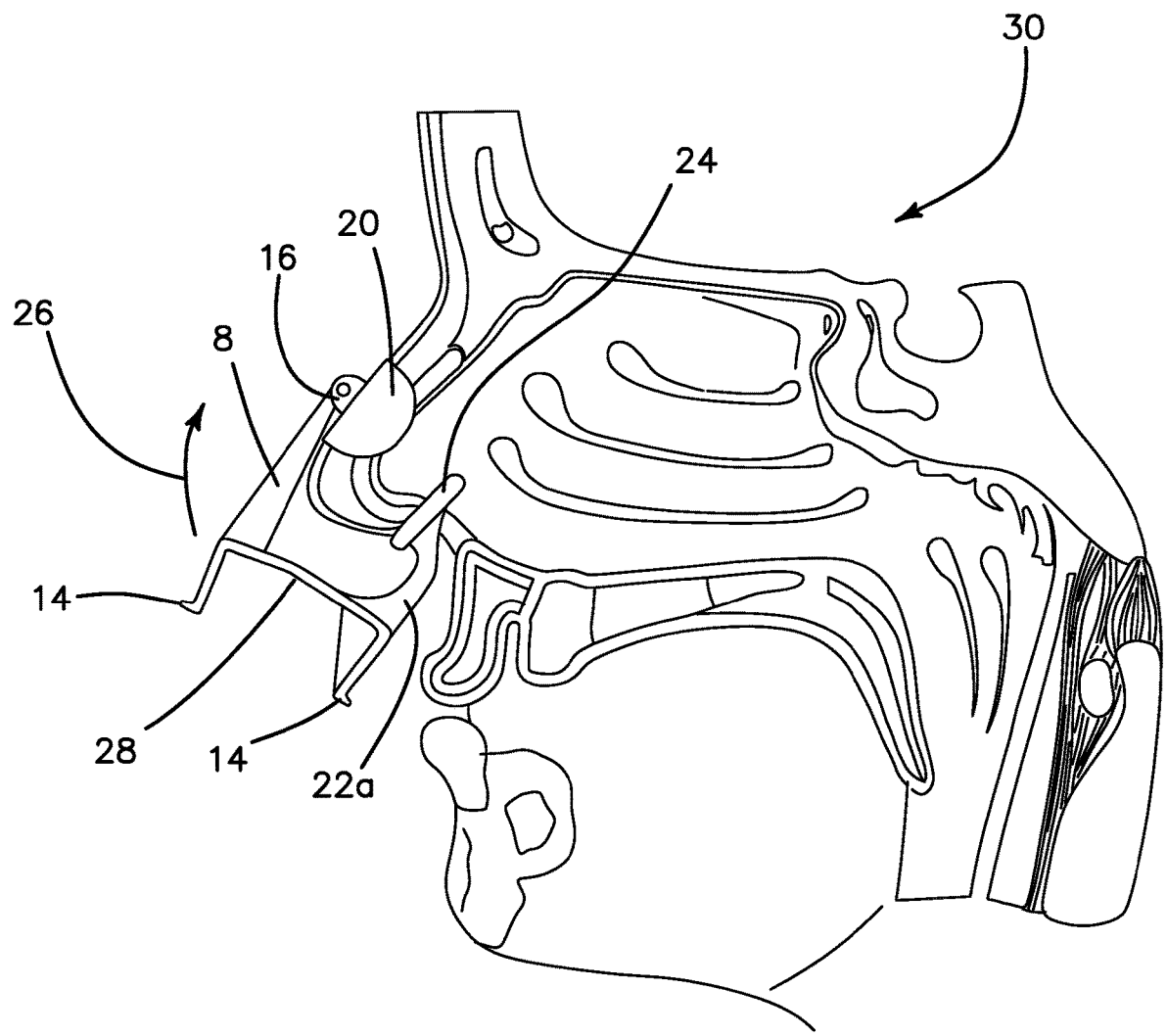
FIG. 5 is a cross sectional view of the nasal compressive device seen in FIG. 1 after it has been applied to a user's nose, specifically wherein a nasal bridge of the nasal compressive device is applied to the dorsum portion of the user's nose and wherein a pair of nasal plugs have been inserted into the user's nostrils.

To apply the nasal compressive device 10, a user 30 in one particular embodiment seen in FIG. 5 applies the nasal compressive device 10 by first bringing the distal end of the nasal compressive device 10 comprising the nasal bridge 20 and nasal plugs 24 into close proximity to the nostrils and tip of the user's nose. The user 30 actuates the finger grips 14 to open the nasal compressive device 10 by separating or creating a gap between the nasal bridge 20 and the nasal plugs 24 and then inserting the narrowed or tapered distal tip of each nasal plug 24 into each corresponding nostril. The user 30 continues to insert each nasal plug 24 through the user's corresponding vestibules until contact is made with an inner surface of the user's nasal cavity. The user 30 may then relax the pressure placed on the finger grips 14 of the clip 12 which in turn closes the nasal compressive device 10 and brings the nasal bridge 20 and nasal plugs 24 closer together with the tip of the user's nose disposed there between. In other words, as the user 30 relaxes the squeezing force placed on the clip 12, the nasal bridge 20 is brought downwards onto a portion of the user's nasal dorsum while at the same time the nasal plugs 24 are brought upwards against the inner surface of the distal portion of the user's nasal cavity. The inherent or natural spring constant of the spring 28 ensures that the nasal compressive device 10 applies a sufficient squeezing force or positive pressure to not only maintain the nasal compressive device 10 in position, on and within the user's nose, but to apply a sufficient upwardly directed force on the lower nasal cartilage of the user 30 as indicated by arrow 26. The upwardly directed force 26 supplied by the nasal compressive device 10 effectively lifts the lower nasal cartilage of the user 30 and prevents fluid from collecting in the tip of the user's nose even when the user 30 may not have their head generally in an elevated position. For example, using the nasal compressive device 10, the user may choose to lay down in a prone position while still applying the upwardly directed force 26 to their lower nasal cartilage, thereby reducing any swelling or fluid accumulation which would otherwise occur during their recovery phase while also further shaping the nose at the same time. The upwardly directed force 26 further ensures that the user's skin is more likely to bond or heal with the newly placed or corrected cartilage of the user's nose. Additionally, while simultaneously providing an upwardly directed force 26, the nasal bridge 20 applies a downward or compressive force over the dorsum of the user which further reduces any post-operative bleeding or fluid collection within the middle and distal portions of the user's nose and thus help prevent poly-beak deformity. To remove the nasal clip 10, the user once again squeezes the finger grips 14 which in turn compresses the spring portion 28 and backs the nasal bridge 20 off of the user's nose, thereby allowing the user to quickly and comfortably remove the nasal plugs 24 from the inside of their nasal cavity. The nasal compressive device 10 may be repeatedly applied and removed in the above manner for as long as treatment is required or until the user has sufficiently recovered from a recent rhinoplasty or any related medical procedure.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. Far example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A nasal compressive device comprising:
   a clip;
   a nasal bridge disposed on a first segment of the clip at a distal end of the first segment, wherein the first segment includes a pivot point disposed on the first segment of the clip, wherein the nasal bridge is rotatably coupled to the first segment of the clip through the pivot point;
   a plurality of nasal plugs disposed on a second segment of the clip, wherein the second segment includes a pair of nasal inserts that are substantially parallel respective to each other, wherein each of the nasal inserts is coupled to a nasal plug of the plurality of nasal plugs at respective distal ends of the nasal inserts; and
   a spring portion disposed between the first segment of the clip comprising the nasal bridge and the second segment of the clip comprising the nasal plugs,
   wherein the spring portion is configured to push the nasal plugs and the nasal bridge together when in an expanded configuration.

2. The nasal compressive device of claim 1 wherein the plurality of nasal plugs disposed on the second segment of the clip are disposed at an angle relative to each other.

3. The nasal compressive device of claim 1 wherein each of the plurality of nasal plugs comprises a longitudinal axis that are disposed in a parallel position relative to each other.

4. The nasal compressive device of claim 1 wherein each of the plurality of nasal plugs comprises a tapered shape comprising a smaller cross-sectional width at a distal end of each of the plurality of nasal plugs relative to a proximal end of each of the plurality of nasal plugs.

5. The nasal compressive device of claim 1 wherein the nasal bridge disposed on the first segment of the dip is configured to accommodate a nasal dorsum of a user.

6. The nasal compressive device of claim 1 further comprising a plurality of finger grips disposed on the dip.

7. The nasal compressive device of claim 6 wherein at least one of the plurality of finger grips is disposed between the first segment of the clip and the spring portion, and wherein at least one other of the plurality of finger grips is disposed between the second segment of the clip and the spring portion.

8. A method for preventing fluid collection in the nose of a user and further shaping the nose post-surgery, the method comprising:
   opening a nasal compressive device of claim 1;
   inserting the nasal plugs into a corresponding pair of nostrils of the user's nose;
   closing the nasal compressive device over the nose of the user; and
   applying an upwardly directed force to a lower nasal cartilage portion of the user's nose.

9. The method of claim 8 further comprising applying a compressive force to a dorsum portion of the user's nose.

10. The method of claim 9 wherein the compressive force and the upwardly directed force are simultaneously applied to the dorsum portion and the distal nasal portion of the user's nose, respectively.

11. The method of claim 9 wherein applying the compressive force to the dorsum portion of the user's nose comprises pressing the nasal bridge disposed on the nasal compressive device against the dorsum portion of the user's nose.

12. The method of claim 11 wherein pressing the nasal bridge disposed on the nasal compressive device against the dorsum portion of the user's nose further comprises expanding the spring portion of the nasal compressive device.

13. The method of claim 11 further comprising changing an angle of the nasal bridge relative to the first segment of the nasal compressive device.

14. The method of claim 8 wherein opening the nasal compressive device comprises compressing the spring portion and separating the nasal bridge from the nasal plugs.

15. The method of claim 14 wherein compressing the spring portion comprises squeezing a pair of finger grips together, wherein each of the pair of finger grips correspond to the first segment and the second segment of the nasal compressive device, respectively.

16. The method of claim 8 wherein applying the upwardly directed force to the lower nasal cartilage portion of the user's nose comprises pressing each of the nasal plugs against an inner surface of a nasal cavity of the user.

17. The method of claim 8 wherein closing the nasal compressive device comprises expanding the spring portion and bringing the nasal bridge closer together to the nasal plugs.

18. The method of claim 8 wherein inserting the nasal plugs disposed on the nasal compressive device into a corresponding pair of nostrils of the user's nose comprises inserting the pair of parallel nasal inserts into the corresponding pair of nostrils of the user's nose.

19. The method of claim 8 wherein inserting the nasal plugs disposed on the nasal compressive device into a corresponding pair of nostrils of the user's nose comprises inserting at least one of the nasal plugs into at least of one of the pair of nostrils at an angle relative to the remaining one of the nasal plugs.

\* \* \* \* \*